United States Patent
Lombardi et al.

[11] Patent Number: 4,769,483
[45] Date of Patent: Sep. 6, 1988

[54] CYCLOALKYL-SUBSTITUTED 4-AMINOPHENYL DERIVATIVES AND PROCESS FOR THEIR PREPARATION

[75] Inventors: Paolo Lombardi, Milan; Angelo Crugnola, Varese; Enrico di Salle, Milan, all of Italy

[73] Assignee: Farmitalia Carlo Erba, S.p.A., Milan, Italy

[21] Appl. No.: 902,873

[22] Filed: Sep. 2, 1986

[30] Foreign Application Priority Data

Sep. 6, 1985 [GB] United Kingdom ............ 8522186

[51] Int. Cl.$^4$ .................................. C07C 101/00
[52] U.S. Cl. .................................. 560/019; 564/168; 564/305; 564/306; 564/336
[58] Field of Search .............. 560/019; 564/168, 583, 564/305, 336

[56] References Cited

FOREIGN PATENT DOCUMENTS 0094599 10/1983 European Pat. Off. .
2223855 12/1972 Fed. Rep. of Germany .
2443342  3/1976 Fed. Rep. of Germany .
2178429  2/1987 United Kingdom .

Primary Examiner—Paul J. Killos
Attorney, Agent, or Firm—Murray and Whisenhunt

[57] ABSTRACT

The invention relates to cycloalkyl substituted 4-aminophenyl derivatives of formula (I)

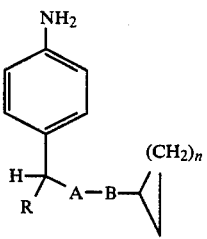

wherein

R is $C_1$–$C_4$ alkyl:
n is an integer of 1 to 5; and either
(a) A is $$\diagup_{\diagdown}C{=}O$$

and B is —O—, —NH— or —CH$_2$—; or
(b) A is —CH$_2$— and B is —O—, —NH—, —CH$_2$— or $$\diagup_{\diagdown}C{=}O;$$

or
(c) A is —O— and B is $$\diagup_{\diagdown}C{=}O$$

or —CH$_2$—; or
(d) A is —NH— and B is $$\diagup_{\diagdown}C{=}O$$

or —CH$_2$— and their pharmaceutically acceptable salts.

The scope of the invention includes also a process for preparing the said compounds of formula (I) and pharmaceutical compositions containing same.

The compounds of the invention show aromatase inhibiting activity and can be useful, e.g., in treating hormone-dependent tumors and prostatic hypertrophy or hyperplasia.

17 Claims, No Drawings

CYCLOALKYL-SUBSTITUTED 4-AMINOPHENYL DERIVATIVES AND PROCESS FOR THEIR PREPARATION

The present invention relates to cycloalkyl-substituted 4-aminophenyl derivatives, to a process for their preparation, to pharmaceutical compositions containing them and to the use of said compounds as inhibitors of the biosynthesis of estrogens, particularly as aromatase inhibitors. Basic and clinical data indicate that estrogens are the hormones involved in the pathogenic cellular changes associated with the growth of some hormone-dependent cancers, such as breast, endometrial and ovarian carcinoma. Estrogens are also involved in the pathogenesis of benign prostatic hyperplasia. It has been envisaged that an effective inhibition of the biosynthesis of estrogens, better if resulting from compounds able to neutralize the activity of the enzyme aromatase which performs the aromatisation of the steroidic ring A, may have useful application for controlling the amount of circulating estrogens, and estrogen-dependent tumors.

Non-steroidal known substances which have been reported to be endowed with a more or less selective aromatase-inhibiting action are, for example, aminoglutethimide [Ann. Surg. 187, 475 (1978); Lancet, 2, 646 (1978)]; 4-cyclohexylaniline [Endocrinology, 114, 2128 (1984)], and 4-pyridyl-3-ethyl-2,6-piperidinedione [J. Med. Chem., 28, 200 (1985)].

The invention provides a new group of non-steroidal substances having aromatase-inhibiting properties, which are cycloalkyl-substituted 4-aminophenyl derivatives having the general formula (I)

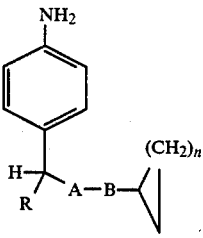

wherein
R is $C_1$–$C_4$ alkyl;
n is an integer of 1 to 5; and either
(a) A is

and B is —O—, —NH— or —CH$_2$—; or
(b) A is —CH$_2$— and B is —O—, —NH—, —CH$_2$— or

or
(c) A is —O— and B is $$\diagdown C=O$$

or —CH$_2$—; or
(d) A is —NH— and B is $$\diagdown C=O$$

or —CH$_2$—.

Also the pharmaceutically acceptable salts of the compounds of formula (I) are included within the scope of the invention. The said salts are the salts with pharmaceutically acceptable acids, both inorganic acids, such as, e.g., hydrochloric and sulfuric, and organic acids such as, e.g., citric, tartaric, maleic, malic, succinic, methanesulfonic and ethanesulfonic. All the possible isomers of formula (I) are included within the scope of the invention, both separately and in mixture. Thus, for example, for each compound of formula (I) two distinct optical isomers, i.e. enantiomers, may exist according to the configuration of the chiral carbon atom carrying the R substituent. The formula (I) is meant to cover both the enantiomers, either separately or in mixture, in particular racemic mixture.

Preferred enantiomers according to the invention are those represented by the formula (Ia)

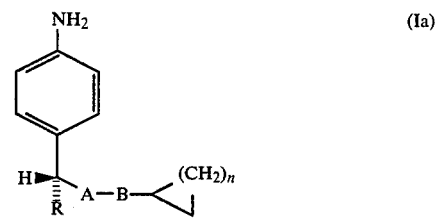

wherein
R, n, A and B are as defined above.

In the above formula (I) the $C_1$–$C_4$ alkyl group is, preferably, methyl or ethyl, especially methyl.
Preferred values for n are 3 and 4, in particular 4.
Preferred salts are the hydrochlorides.
Examples of specific compounds preferred under this invention are the following compounds both as single enantiomers and as mixtures of enantiomers, in particular racemic mixtures:
cyclohexyl 2-(4'-aminophenyl)propionate;
N-cyclohexyl-2-(4'-aminophenyl)propanamide;
2-(4'-aminophenyl)propylcyclohexyl ether;
N-cyclohexyl-2-(4'-aminophenyl)propylamine;
1-cyclohexyl-3-(4'-aminophenyl)-2-butanone;
1-cyclohexyl-3-(4'-aminophenyl)butane;
1-(4'-aminophenyl)ethylcyclohexanecarboxylate;
1-(4'-aminophenyl)ethylcyclohexylmethyl ether;
N-[1-(4'-aminophenyl)ethyl]cyclohexanecarboxyamide;
N-[1-(4'-aminophenyl)ethyl]cyclohexylmethylamine;
2-(4'-aminophenyl)propylcyclohexylketone,
and the pharmaceutically acceptable salts thereof, especially the hydrochlorides.

The compounds of formula (I) may be prepared by a process comprising (1) reacting a compound of formula (II)

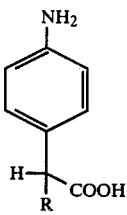 (II)

wherein R is as defined above, or a reactive derivative thereof, with a compound of formula (III)

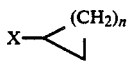 (III)

wherein n is as defined above and X is OH or NH$_2$, so obtaining a compound of formula (I) wherein R and n are as defined above, A is

and B is —O— or —NH— respectively; or (2) reducing a compound of formula (IV)

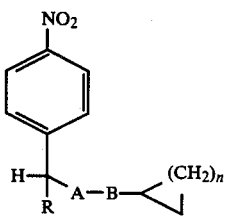 (IV)

wherein R and n are as defined above and either (i) A is

and B is —O—, —NH— or —CH$_2$— or (ii) A is —O—, —NH— or —CH$_2$— and B is

so obtaining a corresponding compound of formula (I) wherein either (i) A is

and B is —O—, —NH— or —CH$_2$— or (ii) A is —O—, —NH— or —CH$_2$— and B is

or (3) reducing a compound of formula (I) wherein R and n are as defined above and either (i) A is

and B is —O— or NH, or (ii) A is —O— or NH and B is

so obtaining a corresponding compound of formula (I) wherein either (i) A is —CH$_2$— and B is —O— or NH or, respectively, (ii) A is —O— or NH and B is —CH$_2$—; or (4) deoxygenating a compound of formula (I) wherein A is

and B is —CH$_2$— or A is —CH$_2$— and B is $$\diagdown C=O,\diagup$$

so obtaining a compound of formula (I) wherein A and B are both —CH$_2$—; and, if desired, salifying the compound of formula (I) or obtaining a free compound of formula (I) from a salt thereof and/or, if desired, separating a mixture of isomers of formula (I) into the single isomers.

The intermediate compounds of the above formulae (III) and (IV) and of the following formulae (V), (VII) and (IX), may be, as the compounds of formula (I), either single enantiomers or mixtures of enantiomers.

A reactive derivative of an aminoacid of formula (II) may be, e.g., an acyl halide, in particular the chloride, of the acid, or the anhydride thereof.

Preferably the reaction between a compound of formula (II) and a compound of formula (III) is performed using a reactive derivative of the compound (II), e.g. of the kind previously specified, and then the reaction is preferably carried out in an inert organic solvent such as, for instance, anhydrous benzene or toluene, in the presence of a base, either an organic base such as, e.g., triethylamine or pyridine, or an inorganic base such as, e.g., an alkali metal, e.g. sodium or potassium hydroxide, carbonate or bicarbonate.

Usual procedures described in organic chemistry for esterification and amidation reactions may be followed.

The reduction of a compound of formula (IV) may be carried out, for instance, by stannous chloride in an inert solvent such as, e.g., methanol, ethanol or ethyl acetate at a temperature ranging between about 40° C. and about 100° C. for a reaction time of about 0.5-3 hours; or by ammonium formate in presence of a hydrogenation catalyst, preferably 10% Pd/C operating in a suitable solvent such as, e.g., an aliphatic alcohol, e.g. methanol or ethanol, preferably at a temperature ranging between about 20° C. and about 50° C. in a reaction time of from about 0.5 hour to about 1 hour; or by hydrogenation in presence of a catalyst, preferably 10% Pd/C, in a solvent such as, e.g., an aliphatic alcohol, in particular methanol or ethanol, at a temperature ranging between about 20° C. and about 50° C. and at a pressure ranging approximately between the atmospheric pressure and 50 psi. The reduction of a compound of formula (I) wherein either (i) A is

and B is —O— or —NH— or (ii) A is —O— or —NH— and B is

is carried out in presence of a reducing agent such as, e.g., LiAlH$_4$ or B$_2$H$_6$ in an inert solvent such as tetrahydrofuran, dioxane, diglyme and similar solvents, preferably at a temperature ranging between about 40° C. and about 120° C. for a reaction time varying approximately in the range of 4-48 hours.

The deoxygenation of a compound of formula (I) wherein A is

and B is —CH$_2$— or A is —CH$_2$— and B is

is preferably carried out by transforming the carbonyl group into the corresponding 1,3-dithiolane according to generally known methods, and then reducing the latter derivative, e.g. by the action of an alkali metal, such as, e.g., lithium or sodium, or calcium, in liquid ammonia, according to known procedures.

Alternatively, the 1,3-dithiolane derivative may be reduced by Raney-Nickel in an inert solvent, such as, e.g., ethanol, dioxane, acetone, at a temperature ranging between about 20° C. and about 80° C. for a reaction time of about 0.5-4 hours, or also by tributyl tin hydride in an inert aprotic solvent, preferably benzene, at a temperature ranging between about 60° C. and about 100° C., for a reaction time of about 1-3 hours. Optionally, the carbonyl group in the compound of formula (I) may be transformed into the corresponding tosylhydrazone by general methods and the derivative so obtained may be reduced by the action of hydrides, for instance with lithium aluminium hydride or bis(benzoyloxy)borane, operating in an inert, aprotic solvent such as, e.g., diethylether, dioxane, tetrahydrofuran, diglyme, chloroform or methylene chloride, at a temperature ranging between about 0° C. and around 40° C. and for reaction times of about 0.5-4 hours; or with sodium cyanoborohydride operating in a protic solvent such as, e.g., methanol, ethanol, or propanol, at a temperature ranging between around 40° C. and around 100° C. for a reaction time of about 1-24 hours.

The optional salification of a compound of formula (I) and the preparation of a free compound of formula (I) from a salt thereof may be performed by conventional known methods. Standard procedures may be followed also for separating a mixture of isomers into the single isomers. In particular, for example, for separating a racemic mixture into the single enantiomers, the mixture may be, e.g., reacted with an optically active acid to give a mixture of diastereoisomeric salts which are separated by means of, e.g., fractional crystallization or chromatography. From each separated diastereoisomeric salt, the single enantiomer of formula (I) may be then recovered in a conventional way.

The compounds of formula (II) and (III) are either known compounds or may be prepared by known methods from known compounds. Also the compounds of formula (IV) can be prepared from known compounds following methods and procedures known in the organic chemistry. In particular, for example, a compound of formula (IV) wherein A is

and B is —O— or —NH— can be prepared reacting a compound of formula (V)

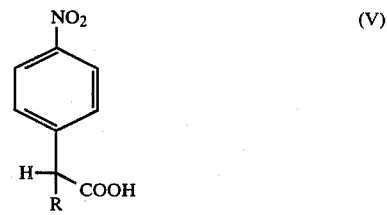

wherein R is as defined above or, preferably, a reactive derivative thereof such as, for instance, a corresponding acyl halide, e.g. chloride, or the anhydride thereof, with a compound of formula (III) as previously defined.

The reaction may be performed under conditions analogous to those reported before in this specification for the reaction between a compound of formula (II) and a compound of formula (III).

A compound of formula (IV) wherein A is

and B is —CH₂— may be prepared, e.g., reacting a compound of formula (V), or a reactive derivative thereof as hereinbefore defined, with a compound of formula (VI)

  (VI)

wherein n is as defined above, M is a metal, preferably Mg, suitable to give a Grignard reagent, and Y is a halogen, preferably bromine, iodine or chloride.

The reaction may be carried out in the usual conditions described in the organic chemistry for the Grignard reactions. A compound of formula (IV) wherein A is —O— or —NH— and B is

may be obtained, e.g., reacting a compound of formula (VII)

  (VII)

wherein R and X are as defined above, with a compound of formula (VIII)

  (VIII)

wherein n is as defined above, or a reactive derivative thereof, e.g. of the kind indicated before for a reactive derivative of a compound of formula (II).

The reaction may be carried out following conditions analogous to those reported above with reference to the reaction between compounds (II) and compounds (III). A compound of formula (IV) wherein A is —CH₂— and B is

may be obtained, e.g., by Grignard reaction between a compound of formula (IX)

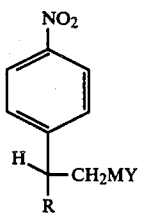  (IX)

wherein R, M and Y are as defined above, and a compound of formula (VIII) or a reactive derivative thereof as before specified.

Conditions usually described in the organic chemistry for the Grignard reactions may be followed.

The compounds having the formulae (V), (VI), (VII), (VIII) and (IX) are known compounds or may be prepared by known methods from known compounds.

The compounds of the invention show aromatase inhibiting activity.

A comparison between their aromatase inhibiting effect in vitro and the aromatase inhibiting effect in vitro of the well-known non-steroidal aromatase inhibitors aminoglutethimide [R. J. Sauten et al., Cancer Research (Suppl.) 42, 3353s, 1982] and 4-cyclohexyl-aniline [J. T. Kellis et al., Endocrinology 114, 2128, 1984], indicates that the compounds of the invention are more potent aromatase inhibitors than the reference compounds.

Thus, for example, the comparison between the in vitro activity of the two compounds of the invention cyclohexyl 2-(R)-2-(4'-aminophenyl)propionate [internal code FCE 24328] and N-cyclohexyl-2-(R)-2-(4'-aminophenyl)propanamide [internal code FCE 24786] and the two above said reference compounds gave the results summarized in the following table.

TABLE

| Inhibition of human placental aromatase in vitro | | |
|---|---|---|
| | Aromatase inhibition | |
| Compound | IC₅₀ (μM) | Relative potency |
| Aminoglutethimide | 2.12 | 1 (by definition) |
| 4-cyclohexylaniline | 1.22 | 1.7 |
| FCE 24328 | 0.10 | 21.2 |
| FCE 24786 | 0.13 | 16.3 |

FCE 24328: Ia, R = CH₃, A = $\diagdown\!\!\!\diagup$ C=O, B = —O—, n = 4;

FCE 24786: Ia, R = CH₃, A = $\diagdown\!\!\!\diagup$ C=O, B = —NH—, n = 4.

The assay of the aromatase inhibition in vitro was carried out as follows: the enzyme system was isolated from the microsomal fraction of human placental tissue according to standard procedure. The assay of Thompson and Siiteri [F. A. Thompson and P. K. Siiteri, J. Biol. Chem. 249, 5364, 1974] which determines the rate of aromatization as measured by the liberation of ³H₂O from 4-[1β,2β-³H]androstene-3,17-dione was used. All incubations were carried out in a shaking water bath at 37° C. in air in 10 mM potassium phosphate buffer, pH 7.5, which contained 100 mM KCl, 1 mM EDTA and 1 mM dithiothreitol.

The experiments were carried out in 1 ml incubation volume containing 50 nM 4-[³H]androstenedione, various concentrations of the inhibitors, 100 μM NADPH and 0.05 mg of microsomal proteins. After 15 minutes of incubation the reaction was stopped by the addition of choroform (5 ml).

After centrifugation at 1500 ×g for 5 minutes aliquots (0.5 ml) were removed from the water phase for determination of ³H₂O formed.

The concentration of each compound required to reduce control aromatase by 50% (IC₅₀) was determined by plotting % inhibition versus log of inhibitor concentration.

The relative potency of each compound versus aminoglutethimide was calculated according to the relation:

$$\text{Relative potency} = \frac{IC_{50} \text{ of aminoglutethimide}}{IC_{50} \text{ of test compound}}$$

In view of the above indicated aromatase inhibiting activity, the compounds of the invention can be useful in all the situations in which a decrease in estrogen synthesis is desirable, in particular in the treatment of the estrogen dependent tumors such as, for instance, pre- and post-menopausal breast tumors, ovarian tumors, endometrial tumors, pancreatic tumors, and prostatic hypertrophy or hyperplasia.

Accordingly, object of the invention is also a method of producing inhibition of the enzyme aromatase and, consequently, because of inhibition of estrogen biosynthesis, a method of treating estrogen-dependent tumors, such as, e.g., breast tumors, ovarian tumors, uterine tumors, pancreatic tumors and also prostatic hypertrophy or hyperplasia, in a patient in need of it, which method comprises administering to the patient an effective amount of a compound of the invention or a pharmaceutical composition containing it.

The compounds of the invention can be administered in a variety of dosage forms, e.g., orally, in the form of tablets, capsules, sugar or film coated tablets, liquid solutions or suspensions; rectally, in the form of suppositories; parenterally, e.g. intramuscularly, or by intravenous injection or infusion.

The dosage depends on the age, weight, conditions of the patient and administration route; for example the dosage adopted for oral administration to adult humans may range from about 10 to about 400 mg pro dose, from 1 to 5 times daily.

As already said the invention includes pharmaceutical compositions comprising a compound of the invention in association with a pharmaceutically acceptable excipient (which can be a carrier or diluent).

The pharmaceutical compositions containing the compounds of the invention are usually prepared following conventional methods and are administered in a pharmaceutically suitable form.

For example, the solid oral forms may contain, together with the active compound, diluents, e.g., lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. a starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes. The liquid dispersions for oral administration may be e.g. syrups, emulsions and suspensions.

The syrups may contain as carrier, for example, saccharose or saccharose with glycerine and/or mannitol and/or sorbitol; in particular a syrup to be administered to diabetic patients can contain as carriers only products not metabolizable to glucose, or metabolizable in very small amount to glucose, for example sorbitol.

The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

The solutions for intravenous injections or infusions may contain as carrier, for example, sterile water or preferably they may be in the form of sterile, aqueous, isotonic saline solutions.

The suppositories may contain together with the active compound a pharmaceutically acceptable carrier, e.g. cocoa-butter, polyethylene glycol, a polyoxyethylene sorbitan fatty acid ester surfactant or lecithin.

The following examples illustrate but do not limit the invention.

When the configuration is unspecified, the compounds are meant to be racemic compounds, i.e. racemates.

EXAMPLE 1

Cyclohexyl 2-(4'-aminophenyl)propionate [I, R=CH$_3$,

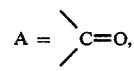

B=—O—, n=]

To a stirred suspension of 2-(4'-aminophenyl)propionic acid (8.25 g, 50 mmole) in dry benzene (100 ml) was added thionyl chloride (30 ml). The resulting mixture was refluxed for 4 hours, cooled and evaporated in vacuo to yield a brown oil. The acyl chloride so obtained, dissolved in dry benzene (50 ml) was then added dropwise to a stirred solution of cyclohexanol (5 g, 50 mmole) and triethylamine (35 ml, 250 mmole) in dry benzene (100 ml) at 5°–10° C. After 3 hrs of additional stirring at room temperature, the reaction mixture was poured into a cold 10% Na$_2$CO$_3$ aqueous solution, the organic phase was separated, washed with water, dried over Na$_2$SO$_4$, filtered and concentrated in vacuo. The resulting residue was purified by fractional distillation. There were obtained 7.10 g (58% yield) of the title compound, b.p. 140°–2° C. (0.05 mm Hg);

Elemental analysis:

calculated % (found %): C 72.84, (72.64); H 8.56, (8.54); N 5.66, (5.72);

NMR (CDCl$_3$, δ): 1.10–1.90 (10H, m); 1.40, (3H, d); 3.10, (2H, br s); 3.57, (1H, q); 4.72, (1H, m); 6.65, (2H, m); 7.10, (2H, m);

IR (CHCl$_3$, cm$^{-1}$): 3460, 3380, 3100, 2980, 2940, 2860, 1720, 1620, 1510.

In analogous fashion one can prepare the single enantiomers of the above title compound as well as the following compounds both as racemates and as single enantiomers:

Cyclohexyl 2-(4'-aminophenyl)butanoate;
Cyclohexyl 2-(4'-aminophenyl)pentanoate;
Cyclopentyl 2-(4'-aminophenyl)propionate, and Cyclopropyl 2-(4'-aminophenyl)propionate.

EXAMPLE 2

Cyclohexyl 2-(R)-2-(4'-aminophenyl)propionate [Ia, R=CH₃,

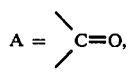

B=—O—, n=4]

To a stirred suspension of (−) 2-(R)-2-(4'-aminophenyl)propionic acid (1.65 g, 10 mmole) in dry benzene (30 ml) was added thionyl chloride (6.0 ml, 80 mmole). The resulting mixture was refluxed for 4 hrs, cooled and evaporated in vacuo to yield a brown oil. The acyl chloride so obtained, dissolved in dry benzene (10 ml) was then added dropwise to a stirred solution of cyclohexanol (5 g, 50 mmole) in dry benzene (15 ml). When the exothermic reaction had ceased, the mixture was refluxed for 2 hrs, cooled and worked up as reported in the Example 1. There were obtained 0.95 g (38% yield) of the title compound, b.p. 140°–2° C. (0.05 mm Hg);

$[\alpha]_D$: +24.6 (c=1, CHCl₃);

Elemental analysis:

calculated % (found %): C 72.84, (72.70); H 8.56, (8.62); N 5.66, (5.63);

NMR (CDCl₃, δ): 1.0–1.9, (10H, m): 1.40, (3H, d); 3.57, (1H, q); 3.60, (2H, br s); 4.72, (1H, m); 6.65, (2H, d); 7.10, (2H, d);

IR (CHCl₃, cm⁻¹): 3600–3200, 2980, 2940, 2860, 1720, 1620, 1520, 1170, 1045.

In analogous manner the following compounds can be prepared:
cyclohexyl 2-(R)-2-(4'-aminophenyl)butanoate;
cyclohexyl 2-(R)-2-(4'-aminophenyl)pentanoate;
cyclopentyl 2-(R)-2-(4'-aminophenyl)propionate, and
cyclopropyl 2-(R)-2-(4'-aminophenyl)propionate.

EXAMPLE 3

N-cyclohexyl-2-(4'-aminophenyl)propanamide [I, R=CH₃,

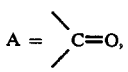

B=—NH—, n=4]

The acyl chloride, prepared from 1.65 g of 2-(4'-aminophenyl)propionic acid and 6 ml of thionyl chloride as reported in the Example 1, was dissolved in dry benzene (15 ml) and added dropwise to a stirred solution of cyclohexylamine (3 g, 30 mmole) in dry benzene (30 ml) at 5°–10° C. After 3 hrs of additional stirring at room temperature the reaction mixture was worked up as reported in the Example 1. The crude product was purified by flash column chromatography on silica gel eluting with chloroform:methanol 98:2 and by recrystallisation from benzene:n-hexane 1:1. There were obtained 1.30 g (53% yield) of the title compound, m.p. 104°–6° C., Elemental analysis:

calculated % (found %): C 73.13, (73.45); H 9.00, (9.02); N 11.37, (11.43);

NMR (CDCl₃, δ): 0.8–2.00 (10H, m); 1.46, (3H, d); 3.42, (1H, q); 3.65, (2H, br s); 5.14, (1H, br s); 6.66, (2H, d); 7.07, (2H, d);

IR (KBr, cm⁻¹): 3600–3100, 3040, 3010, 2920, 2840, 1635.

In analogous fashion one can prepare the single enantiomers of the above title compound as well as the following compounds both as racemates and as single enantiomers:
N-cyclohexyl 2-(4'-aminophenyl)butanamide;
N-cyclohexyl 2-(4'-aminophenyl)pentanamide;
N-cyclopentyl 2-(4'-aminophenyl)propanamide, and
N-cyclopropyl 2-(4'-aminophenyl)propanamide.

EXAMPLE 4

N-cyclohexyl-2-(R)-2-(4'-aminophenyl)propanamide [Ia, R=CH₃,

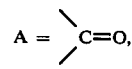

B=—NH—, n=4]

The acyl chloride, prepared from 10 g (60 mmole) of 2-(R)-2-(4'-aminophenyl)propionic acid and 17.5 ml of thionyl chloride as reported in the Example 1, was dissolved in dry benzene (50 ml) and added dropwise to a stirred solution of cyclohexylamine (23.8 g) in dry benzene (200 ml) at 5°–10° C. After 3 hours of additional stirring at room temperature, the reaction was worked up and the product purified as reported in the Example 3. There was obtained 14.75 g (80% yield) of the title compound, m.p. 106°–8° C.;

$[\alpha]_D$: +6.14 (c=1, HCl 0.1N)

Elemental analysis:

calculated % (found %): C 73.13, (73.03); H 9.00, (9.05); N 11.37, (11.25).

In analogous fashion the following compounds can be prepared:
N-cyclohexyl-2-(R)-2-(4'-aminophenyl)butanamide;
N-cyclohexyl-2-(R)-2-(4'-aminophenyl)pentanamide;
N-cyclopentyl-2-(R)-2-(4'-aminophenyl)propanamide;
N-cyclopropyl-2-(R)-2-(4'-aminophenyl)propanamide.

EXAMPLE 5

2-(4'-aminophenyl)propylcyclohexyl ether [I, R=CH₃, A=—CH₂—,

B=—O—, n=4]

To a stirred suspension of lithium aluminum hydride (2.5 g) in anhydrous tetrahydrofuran (50 ml) was added a mixture of cyclohexyl 2-(4'aminophenyl)propionate (3.70 g, 15 mmole), prepared as described in the Example 1, and borontrifluoride etherate (30 ml) in anhydrous tetrahydrofuran (50 ml) dropwise with external cooling. After 3 hrs at 45° C., the reaction mixture was carefully decomposed by adding water, followed by a 23% hydrochloric acid solution. Most of the organic solvent was evaporated in vacuo, the aqueous solution was brought to pH 9 by adding a concentrated sodium hydroxide solution and extracted with diethyl ether (3 times). The combined extracts were washed with water to neutral, dried over Na₂SO₄ and evaporated in vacuo. The resulting residue was purified by column chromatography on silica gel eluting with benzene:ethyl acetate 95:5 and by fractional distillation. There were obtained 2.3 g (65% yield) of the title compound, b.p. 125°–127° C. (0.05 mm Hg), Elemental analysis:
calculated % (found %): C 77.20, (77.28); H 9.94, (9.95); N 6.00, (6.01);
NMR (CDCl$_3$, δ): 1.10–1.90 (10H, m); 1.25, (3H, d); 2.86, (1H, m); 3.18, (1H, m); 3.40, (2H, m); 4.50, (2H, br s); 6.60, (2H, m); 7.02, (2H, m);
IR (CHCl$_3$, cm$^{-1}$): 3440, 3360, 3080, 3020, 2920, 2840, 1610, 1510, 1175, 1130, 1075.

In analogous fashion one can prepare the single enantiomers of the above title compound as well as the following compounds both as racemates and as single enantiomers:
2-(4'-aminophenyl)butylcyclohexyl ether;
2-(4'-aminophenyl)pentylcyclohexyl ether;
2-(4'-aminophenyl)propylcyclopentyl ether, and
2-(4'-aminophenyl)propylcyclopropyl ether.

EXAMPLE 6

2-(R)-2-(4'-aminophenyl)propylcyclohexyl ether [Ia, R=CH$_3$, A=—CH$_2$—, B=—O—, n=4]

To a stirred suspension of lithium aluminum hydride (2.5 g) in anhydrous tetrahydrofuran (50 ml) was added a mixture of cyclohexyl 2-(R)-2-(4'-aminophenyl)propionate (3.07 g, 12.4 mmole), prepared as described in Example 2, and borontrifluoride etherate (30 ml) in anhydrous tetrahydrofuran (50 ml) dropwise with external cooling. After 3 hours at 45° C., the reaction mixture was worked up and the product purified as reported in the Example 5.

There were obtained 1.04 g (36%) of the title compound,
b.p. 120° C. (0.05 mm Hg);
[α]$_D$: +12.5 [c=1, CHCl$_3$];
Elemental analysis:
calculated % (found %): C 77.20, (77.27); H 9.94, (9.98); N 6.00, (6.03).

In analogous fashion the following compounds can be prepared:
2-(R)-2-(4'-aminophenyl)butylcyclohexyl ether;
2-(R)-2-(4'-aminophenyl)pentylcyclohexyl ether;
2-(R)-2-(4'-aminophenyl)propylcyclopentyl ether;
2-(R)-2-(4'-aminophenyl)propylcyclopropyl ether.

EXAMPLE 7

N-cyclohexyl-2-(4'-aminophenyl)propylamine bis hydrochloride [I, R=CH$_3$, A=—CH$_2$—, B=—NH—, n=4]

To a stirred suspension of lithium aluminum hydride (0.4 g) in anhydrous diglyme (10 ml) was added N-cyclohexyl 2-(4'-aminophenyl)propanamide (0.482, 2 mmole), prepared as described in the Example 3, dissolved in anhydrous diglyme (5 ml) dropwise and under nitrogen atmosphere. The reaction mixture was then heated at 85°–95° C. for 6 hrs. After cooling, the excess of lithium aluminum hydride was decomposed by the careful addition of a mixture of methanol, t-butylmethylether and water. The organic phase was separated, washed with water, dried over Na$_2$SO$_4$ and filtered. The filtrate was saturated with anhydrous hydrogen chloride and the resulting precipitate was filtered off and recrystallized from methanol:isopropanol 1:2.

There were obtained 0.5 g (82% yield) of the title compound as bis hydrochloride,
Elemental analysis:
calculated % (found %): C 59.01, (58.72); H 8.58, (8.65); N 9.18, (9.08); Cl 23.23, (22.85);
IR (KBr, cm$^{-1}$): 3100–2300, 2920, 2840, 1610, 1505, 1450, 1375;
m/e: 232, 112.

In analogous fashion one can prepare the single enantiomers of the above title compound as well as the following compounds both as racemates and as single enantiomers:
N-cyclohexyl-2-(4'-aminophenyl)butylamine;
N-cyclohexyl-2-(4'-aminophenyl)pentylamine;
N-cyclopentyl-2-(4'-aminophenyl)propylamine, and
N-cyclopropyl-2-(4'-aminophenyl)propylamine.

EXAMPLE 8

Cyclohexyl 2-(4'-nitrophenyl)pentanoate [IV, R=CH$_3$CH$_2$CH$_2$,

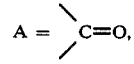

B=—O—, n=4]

To a stirred suspension of 2-(4'-nitrophenyl)pentanoic acid (3.35 g, 15 mmole) in dry benzene (40 ml) was added thionyl chloride (6.0 ml). The resulting mixture was refluxed for 4 hrs, cooled and evaporated in vacuo to yield a brown oil. The acyl chloride so obtained, dissolved in dry benzene (25 ml), was then added dropwise to a stirred solution of cyclohexanol (1.5 g, 15 mmole) and triethylamine (4.2 ml, 30 mmole) in dry benzene (50 ml) at 5°–10° C. After 3 hrs of additional stirring at room temperature, the reaction mixture was treated with water (100 ml); the organic phase was separated, washed with water, a diluted NaHSO$_4$ aqueous solution, a 8% NaHCO$_3$ aqueous solution, and water, then dried over Na$_2$SO$_4$, filtered and concentrated in vacuo. There were obtained 3.07 g of the crude title compound as a brown oil,
IR (CHCl$_3$, cm$^{-1}$): 1725, 1520, 1350.

In analogous fashion one can prepare the single enantiomers of the above title compound as well as the following compounds both as racemates and as single enantiomers:
cyclohexyl 2-(4'-nitrophenyl)propionate;
cyclohexyl 2-(4'-nitrophenyl)butanoate;
cyclopentyl 2-(4'-nitrophenyl)pentanoate and
cyclopropyl 2-(4'-nitrophenyl)pentanoate.

EXAMPLE 9

Cyclohexyl 2-(4'-aminophenyl)pentanoate [I, R=CH$_3$CH$_2$CH$_2$,

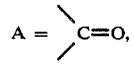

B=—O—, n=4]

A stirred mixture of 3.05 g of crude cyclohexyl 2-(4'-nitrophenyl)pentanoate and 300 mg of 10% Pd/C catalyst in 75 ml of 95% ethanol was hydrogenated in a Brown-type automatic hydrogenator at room temperature till the uptake of hydrogen ceased.

The catalyst was filtered off and the filtrate was evaporated in vacuo.

The resulting residue was purified by fractional distillation.

There were obtained 1.25 g of the title compound, b.p. 150°–5° C. (0.05 mm Hg);

Elemental analysis:

calculated % (found %): C 74.14, (73.67); H 9.15, (9.12); N 5.09, (5.37);

NMR (CDCl$_3$, δ): 0.80–2.30 (14H, m); 0.90, (3H, t); 3.40, (1H, t); 3.50, (2H, br s); 4.75, (1H, m); 6.59, (2H, m); 7.10, (2H, m);

IR (CHCl$_3$, cm$^{-1}$): 3460, 3380, 3020, 2920, 2850, 1715, 1615, 1510, 1170.

m/e: 275, 148.

In analogous fashion one can prepare the single enantiomers of the above title compound as well as the following compounds both as racemates and as single enantiomers:

cyclohexyl 2-(4'-aminophenyl)propionate;
cyclohexyl 2-(4'-aminophenyl)butanoate;
cyclopentyl 2-(4'-aminophenyl)pentanoate and
cyclopropyl 2-(4'-aminophenyl)pentanoate.

EXAMPLE 10

1-cyclohexyl-3-(4'-nitrophenyl)-2-butanone [IV, R=CH$_3$,

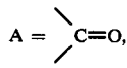

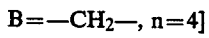

B=—CH$_2$—, n=4]

To a stirred solution of cyclohexylmethyl magnesium iodide (prepared from 7.5 g of cyclohexylmethyl iodide and 0.7 g of magnesium turnings) in anhydrous diethyl ether (30 ml) cooled at 0° C. there was added pulverized anhydrous cadmium chloride (2.6 g) in small portions over a period of 45 min. After one hour of additional stirring at room temperature, the resulting solution was cooled at −70° C. and treated with the dropwise addition of 2-(4'-nitrophenyl)propionyl chloride (prepared from 3.9 g, 20 mmole, of 2-(4'-nitrophenyl)propionic acid and 8.0 ml of thionyl chloride) in anhydrous diethyl ether (10 ml). After one hour of additional stirring, the reaction mixture was carefully decomposed by the dropwise addition of 50 ml of water. The organic phase was separated, the aqueous phase was extracted with diethylether (3 times), the combined extracts were dried over Na$_2$SO$_4$, filtered and concentrated in vacuo. There were obtained 4.1 g of the crude title compound, IR (CHCl$_3$, cm$^{-1}$): 1715, 1520, 1350.

In analogous fashion one can prepare the single enantiomers of the above title compound as well as the following compounds both as racemates and as single enantiomers:

1-cyclohexyl-3-(4'-nitrophenyl)-2-pentanone;
1-cyclohexyl-3-(4'-nitrophenyl)-2-hexanone;
1-cyclopentyl-3-(4'-nitrophenyl)-2-butanone; and
1-cyclopropyl-3-(4'-nitrophenyl)-2-butanone.

EXAMPLE 11

1-cyclohexyl-3-(4'-aminophenyl)-2-butanone [I, R=CH$_3$,

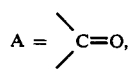

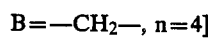

B=—CH$_2$—, n=4]

4.1 g of crude cyclohexyl-3-(4'-nitrophenyl)-2-butanone were reduced and worked up as described in the Example 9. The resulting residue was purified by fractional distillation.

There were obtained 2.2 g of the title compound, b.p. 125°–127° C. (0.05 mm Hg).

Elemental analysis:

calculated % (found %): C 78.36, (78.15); H 9.38, (9.35); N 5.71; (5.80);

IR (CHCl$_3$, cm$^{-1}$): 3460, 3380, 1710, 1620, 1510

In analogous fashion one can prepared the single enantiomers of the above title compound as well as the following compounds both as racemates and as single enantiomers:

1-cyclohexyl-3-(4'-aminophenyl)-2-pentanone;
1-cyclohexyl-3-(4'-aminophenyl)-2-hexanone;
1-cyclopentyl-3-(4'-aminophenyl)-2-butanone; and
1-cyclopropyl-3-(4'-aminophenyl)-2-butanone.

EXAMPLE 12

1-cyclohexyl-3-(4'-aminophenyl)butane [I, R=CH$_3$, A=B=—CH$_2$—, n=4]

To a solution of 1-cyclohexyl-3-(4'-aminophenyl)-2-butanone (2.45 g, 10 mmole) in methylene chloride (50 ml) there were added ethanedithiol (2 ml) and boron trifluoride etherate (2 ml). The mixture was stirred at room temperature during 2 hours, then it was washed with water, a 8% NaHCO$_3$ aqueous solution and water, then dried over CaCl$_2$, filtered and evaporated in vacuo. The crude thioketal so obtained (3.2 g) was dissolved in anhydrous tetrahydrofuran (30 ml) and stirred in presence of Raney nickel (10 g) (prepared according to Org. Synth., 3, 181) for 2 hours at room temperature. The catalyst was filtered off and washed with methylene chloride.

The combined filtrate and washings were evaporated in vacuo to yield a residue which was purified by fractional distillation.

There were obtained 1.4 g (60% yield) of the title compound, b.p. 120°–123° C. (0.05 mm Hg).

Elemental analysis:

calculated % (found %) C 83.11, (83.15); H 10.82, (10.90); N 6.06, (6.07);

IR (CHCl$_3$, cm$^{-1}$): 3440, 3360, 3080, 3020, 2920, 2840, 1610, 1510.

In analogous fashion one can prepare the single enantiomers of the above title compound as well as the following compounds both as racemates and as single enantiomers:

1-cyclohexyl-3-(4'-aminophenyl)pentane;
1-cyclohexyl-3-(4'-aminophenyl)hexane;
1-cyclopentyl-3-(4'-aminophenyl)butane; and
1-cyclopropyl-3-(4'-aminophenyl)butane.

EXAMPLE 13

1-(4'-nitrophenyl)ethyl cyclohexanecarboxylate [IV, R=CH₃, A=—O—,

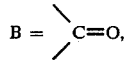

n=4]

To a stirred suspension of cyclohexanecarboxylic acid (1.43 g, 15 mmole) in dry benzene (40 ml) was added thionyl chloride (6.0 ml). The resulting mixture was refluxed for 4 hours, cooled and evaporated in vacuo to yield a brown oil. The acyl chloride so obtained, dissolved in dry benzene (15 ml), was then added dropwise to a stirred solution of 1-(4'-nitrophenyl)ethanol (2.5 g, 15 mmole) and triethylamine (4.2 ml, 30 mmole) in dry benzene (50 ml) at 5°–10° C.

After 3 hours of additional stirring at room temperature, the reaction mixture was worked up as described in the Example 8. There were obtained 1.25 g of the crude title compound as a brown oil, IR (CHCl₃, cm⁻¹): 1725, 1520, 1350.

In analogous fashion the single enantiomers of the title compound can be prepared.

EXAMPLE 14

1-(4'-aminophenyl)ethyl cyclohexanecarboxylate [I, R=CH₃, A=—O—,

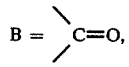

n=4 ]

A stirred mixture of 1.25 g of crude 1-(4'-nitrophenyl)ethyl cyclohexanecarboxylate was hydrogenated as described in the Example 9. There were obtained 0.8 g of the title compound, b.p. 138°–140° C. (0.05 mm Hg).

Elemental Analysis:

calculated % (found %): C 72.84, (72.70); H 8.56, (8.60); N 5.66, (5.61);

IR (CHCl₃, cm⁻¹): 3460, 3380, 3100, 2980, 2860, 1720, 1620, 1510.

In analogous fashion the single enantiomers of the title compound can be prepared.

EXAMPLE 15

1-(4'-aminophenyl)ethylcyclohexylmethyl ether [I, R=CH₃, A=—O—, B=—CH₂—, n=4]

2.46 g (10 mmole) of 1-(4'-aminophenyl)ethylcyclohexanecarboxylate were reduced and worked up as described in the Example 5. There were obtained 1.5 g (61% yield) of the title compound, b.p. 124°–126° C. (0.05 mm Hg);

Elemental analysis:

calculated % (found %): C 77.20, (77.31); H 9.94, (9.93); N, 6.00, (6.02);

IR (CHCl₃, cm⁻¹): 3440, 3360, 1610, 1510, 1175, 1130, 1075.

In analogous fashion the single enantiomers of the title compound can be prepared.

EXAMPLE 16

N-(1R)-[1-(4'-nitrophenyl)ethyl]cyclohexanecarboxamide [IV, R=—CH₃—, A=—NH—,

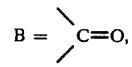

n=4; single enantiomer]

The acyl chloride, prepared from 1.43 g of cyclohexanecarboxylic acid and 6 ml of thionyl chloride as reported in the Example 13, was dissolved in dry benzene (15 ml) and added dropwise to a stirred solution of R-1-(4'-nitrophenyl)ethylamine (7.47 g, 45 mmole) in dry benzene (45 ml) at 5°–10° C. After 3 hours of addition stirring at room temperature, the reaction mixture was poured into cold water, the organic phase was separated, washed with a cold 10% HCl aqueous solution, with water to neutral, dried over Na₂SO₄, filtered and concentrated in vacuo. After crystallization from benzene:cyclohexane 2:1, there were obtained 2.9 g of the title compound, m.p. 161°–3° C.;

[α]_D: +94.3° (c=1, MeOH);

Elemental analysis:

calculated % (found %) C 65.28, (65.19); H 7.31, (7.29); N 10.16, (10.14);

NMR (CDCl₃, δ): 1.48, (3H, d); 5.15, (1H, m); 5.70, (1H, br); 7.43, (2H, dd); 8.18, (2h, dd);

IR (CHCl₃, cm⁻¹): 3435, 3330, 1660, 1510, 1345.

In analogous fashion one can prepare the other enantiomer N-(1S)-[1-(4'-nitrophenyl)ethyl]cyclohexanecarboxamide, m.p. 161°–3° C.,

[α]_D: −93.4° (c=1, MeOH);

Elemental analysis:

calculated % (found %): C 65.07, (65.19); H 7.25, (7.29); N 10.06, (10.14);

as well as the corresponding racemic compound.

EXAMPLE 17

N-(1R)-[1-(4'-aminophenyl)ethyl]cyclohexanecarboxyamide [Ia, R=CH₃, A=—NH—,

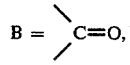

n=4 ]

A stirred mixture of 1.5 g (5.4 mmole) of N-(1R)-[1-(4'-nitrophenyl)ethyl]cyclohexanecarboxyamide was hydrogenated as described in the Example 9. The crude product was crystallized from benzene. There were obtained 1.29 g (92% yield) of the title compound, m.p. 137°–8° C.

[α]_D: +133.4° (c=1, MeOH)

Elemental analysis:

calculated % (found %): C 73.13, (73.01); H 9.00, (9.03); N 11.37, (11.21);

NMR (CDCl₃, δ): 1.44, (3H, d); 3.60 (2H, br, s); 5.02, (1H, m); 5.50, (1H, d); 6.62, (2H, dd); 7.10, (2H, dd);

IR (CHCl₃, cm⁻¹): 3440, 3395, 1660, 1650, 1620, 1490.

In analogous fashion one can prepare the other enantiomer N-(S)-[1-(4′-aminophenyl)ethyl]cyclohexanecarboxyamide, m.p. 137°-8° C. [α]$_D$: −133.4° (c=1, MeOH)

Elemental analysis:
calculated % (found %): C 73.13, (72.98); H 9.00, (9.08); N 11.37, (11.17);
as well as the corresponding racemic compound.

EXAMPLE 18

N-[1-(4′-aminophenyl)ethyl]cyclohexylmethylamine bis hydrochloride [I, R=CH$_3$, A=—NH—, B=—CH$_2$—, n=4]

1 g (4.06 mmole) of N-[1-(4′-aminophenyl)ethyl]cyclohexanecarboxyamide was reduced and worked up as described in the Example 7. There were obtained 0.990 g of the title compound as bis hydrochloride.

Elemental analysis:
calculated % (found %): C 59.01, (58.80); H 8.58, (8.70); N 9.18, (9.00); Cl 23.23, (22.80);
Ir (KBr, cm$^{-1}$): 3100–2300, 2920, 2840, 1610, 1605, 1450, 1375.

In analogous fashion the single enantiomers of the title compound can be obtained.

EXAMPLE 19

2-(4′-aminophenyl)propylcyclohexyl ketone [I, R=CH$_3$, A=—CH$_2$—,

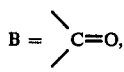

n=4]

The title compound was prepared in 52% overall yield starting from 2-(4′-nitrophenyl)propyl magnesium iodide, cadmium chloride and cyclohexanecarboxyl chloride according to the procedures described in the Examples 10 and 11, b.p.: 123°–125° C. (0.05 mm Hg).

Elemental analysis:
calculated % (found %): C 78.36, (78.20); H 9.38, (9.41); N 5.71, (5.82);
IR (CHCl$_3$, cm$^{-1}$): 3460, 3380, 1710, 1520, 1510.

In analogous fashion the single enantiomers of the title compound can be obtained.

EXAMPLE 20

Tablets, each weighing 0.150 g and containing 25 mg of the active substance, can be manufactured as follows:

| Composition (for 10,000 tablets) | |
| --- | --- |
| Cyclohexyl 2-(R)-2-(4′-aminophenyl)propionate | 250 g |
| Lactose | 800 g |
| Corn starch | 415 g |
| Talc powder | 30 g |
| Magnesium stearate | 5 g |

The cyclohexyl 2-(R)-2-(4′-aminophenyl)propionate, the lactose and half the corn starch are mixed; the mixture is then forced through a sieve of 0.5 mm mesh size. Corn starch (10 g) is suspended in warm water (90 ml) and the rsulting paste is used to granulate the powder. The granulate is dried, comminuted on a sieve of 1.4 mm mesh size, then the remaining quantity of starch, talc and magnesium stearate is added, carefully mixed and processed into tablets.

We claim:

1. A pharmaceutical composition comprising an inert carrier and/or diluent and, as the active substance, an effective amount of a compound of formula (I)

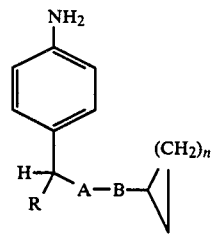

wherein
R is C$_1$–C$_4$ alkyl;
n is an integer of 1 to 5; and either
(a) A is

and B is —O—, —NH— or —CH$_2$—; or
(b) A is —CH$_2$— and B —O—, —NH—, —CH$_2$— or

or
(c) A is —O— and B is

or —CH$_2$—; or
(d) A is —NH— and B is

or —CH$_2$—;
or a pharmaceutically acceptable salt thereof.

2. A pharmaceutical composition according to claim 1, wherein the active substance is a compound, either as single enantiomer or as racemic mixture, selected from the group consisting of:
cyclohexyl-2-(4′-aminophenyl)propionate;
N-cyclohexyl-2-(4′-aminophenyl)propanamide;
2-(4′-aminophenyl)propylcyclohexyl ether;
N-cyclohexyl-2-(4′-aminophenyl)propylamine;
1-cyclohexyl-3-(4′-aminophenyl)-2-butanone;
1-cyclohexyl-3-(4′-aminophenyl)butane;
1-(4′-aminophenyl)ethylcyclohexanecarboxylate;
1-(4′-aminophenyl)ethylcyclohexylmethyl ether;
N-[1-(4′-aminophenyl)ethyl]cyclohexancarboxyamide;

N-[1-(4'-aminophenyl)ethyl]cyclohexylmethylamine;
2-(4'-aminophenyl)propylcyclohexylketone,
or a pharmaceutically acceptable salt thereof.

3. A compound having the formula (I) reported in claim 1 or a pharmaceutically acceptable salt thereof for use as aromatase inhibitor and in the treatment of hormone-dependent tumors and of prostatic hypertrophy or hyperplasia.

4. A pharmaceutical composition according to claim 1 for use as aromatase inhibitor and in the treatment of hormone-dependent tumors and of prostatic hypertrophy or hyperplasia.

5. The use of a compound having the formula (I) reported in claim 1, or a pharmaceutically acceptable salt thereof, in the preparation of a pharmaceutical composition according to claim 1 having activity in inhibiting aromatase and in the treatment of hormone-dependent tumors and prostatic hypertrophy or hyperplasia.

6. Method of producing inhibition of the enzyme aromatase in a patient in need of it, which method comprises administering to the patient an effective amount of a compound having the formula (I) reported in claim 1, or a pharmaceutically acceptable salt thereof.

7. Method of producing inhibition of the enzyme aromatase in a patient in need of it, which method comprises administering to the patient an effective amount of a composition according to claim 1.

8. Method of treating estrogen-dependent tumors or prostatic hypertrophy or hyperplasia in a patient in need of it, which method comprises administering to the patient an effective amount of a compound having the formula (I) reported in claim 1 or a pharmaceutically acceptable salt thereof.

9. Method of treating estrogen-dependent tumors or prostatic hypertrophy or hyperplasia in a patient in need of it, which method comprises administering to the patient an effective amount of a composition according to claim 1.

10. Method according to claim 8 wherein the estrogen-dependent tumor is a breast tumor or an ovarian tumor or an endometrial tumor or a pancreatic tumor.

11. Method according to claim 9 wherein the estrogen-dependent tumor is breast tumor or an ovarian tumor or an endometrial tumor or a pancreatic tumor.

12. A cycloalkyl-substituted 4-aminophenyl derivative of formula (IX)

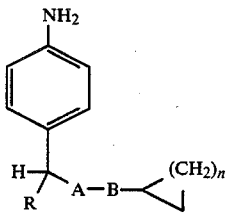
(IX)

wherein
R is $C_1$-$C_4$ alkyl;
n is an integer of 1 to 5; and either
(a) A is

and B is —NH— or —CH$_2$—; or (b) A is —CH$_2$— and B is —O—, —NH—, —CH$_2$' or

or
(c) A is —O— and B is

or —CH$_2$—; or
(d) A is —NH— and B is

or —CH$_2$—;
and the pharmaceutically acceptable salts thereof.

13. A compound according to claim 12 wherein the cycloalkyl-substituted 4-aminophenyl derivative is the enantiomer having the formula (Ia)

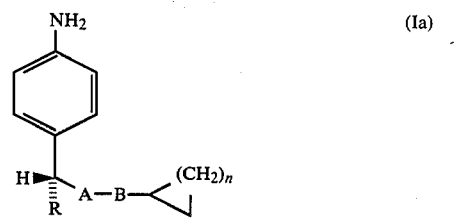
(Ia)

wherein R, n, A and B are as defined in claim 12.

14. A compound according to claim 12 or 13, wherein R is methyl or ethyl and n is 3 or 4.

15. A compound, either as single enantiomer or as racemic mixture, selected from the group consisting of:
N-cyclohexyl-2-(4'-aminophenyl)propanamide;
2-(4'-aminophenyl)propylcyclohexyl ether;
N-cyclohexyl-2-(4'-aminophenyl)propylamine:
1-cyclohexyl-3-(4'-aminophenyl)-2-butanone;
1-cyclohexyl-3-(4'-aminophenyl)butane;
1-(4'-aminophenyl)ethyl cyclohexanecarboxylate;
1-(4'-aminophenyl)ethyl cyclohexylmethyl ether;
N-[1-(4'-aminophenyl)ethyl]cyclohexanecarboxyamide;
N-[1-(4'-aminophenyl)ethyl]cyclohexylmethylamine;
2-(4'-aminophenyl)propylcyclohexylketone
and the pharmaceutically acceptable salts thereof.

16. A process for the preparation of a compound of formula (I)

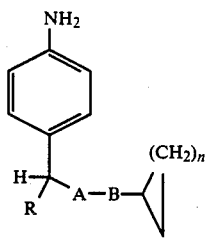

wherein
R is $C_1$-$C_4$ alkyl;
n is an integer of 1 to 5; and either
(a) A is

and B is —O—, —NH— or —CH$_2$—; or
(b) A is —CH$_2$— and B is —O—, —NH—, —CH$_2$— or

or
(c) A is —O— and is

or —CH$_2$—; or
(d) A is —NH— and B is

or —CH$_2$—;
or a pharmaceutically acceptable salt thereof, the process comprising:
(1) reacting a compound of formula (II)

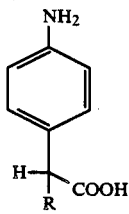

wherein R is as defined above, or a reactive derivative thereof, with a compound of formula (III)

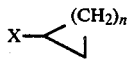

wherein n is as defined above and X is OH or NH$_2$, so obtaining a compound of formula (I) wherein R and n are as defined above, A is

and B is —O— or —NH— respectively; or
(2) reducing a compound of formula (IV)

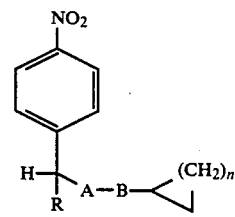

wherein R and n are as defined above and either (i) A is

and B is —O—, —NH— or —CH$_2$— or (ii) A is —O—, —NH— or —CH$_2$— and B is

so obtaining a corresponding compound of formula (I) wherein either (i) A is

and B is —O— —NH— or —CH$_2$— or (ii) A is —O—, —NH— or —CH$_2$— and B is

or
(3) reducing a compound of formula (I) wherein R and n are as defined above and either (i) A is

and B is —O— or NH, or (ii) A is —O— or NH and B is

so obtaining a corresponding compound of formula (I) wherein either (i) A is —CH₂— and B is —O— or NH or, respectively, (ii) A is —O— or NH and B is —CH₂—; or (4) deoxygenating a compound of formula (I) wherein A is

and B is —CH₂— or A is —CH₂— and B is

so obtaining a compound of formula (I) wherein A and B are both —CH₂—; and if desired, salifying the compound of formula (I) or obtaining a free compound of formula (I) from a salt thereof and/or, if desired, separating a mixture of isomers of formula (I) into the single isomers.

17. A compound having the formula (IV) reported in claim 16 wherein either (i) A is $$\diagdown\!\!\!\!\!\diagup C\!=\!O$$

and B is —NH— or —CH₂— or (ii) A is —O—, —NH— or —CH₂— and B is

* * * * *